US009446207B2

(12) United States Patent
Jung

(10) Patent No.: US 9,446,207 B2
(45) Date of Patent: Sep. 20, 2016

(54) NOZZLE UNIT AND DISPENSER

(71) Applicant: Timo Jung, Gottmadingen (DE)

(72) Inventor: Timo Jung, Gottmadingen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 367 days.

(21) Appl. No.: 13/748,810

(22) Filed: Jan. 24, 2013

(65) Prior Publication Data

US 2013/0192593 A1 Aug. 1, 2013

(30) Foreign Application Priority Data

Jan. 27, 2012 (DE) ........................ 10 2012 201 178

(51) Int. Cl.

| | |
|---|---|
| ***A61M 11/00*** | (2006.01) |
| ***B05B 1/14*** | (2006.01) |
| ***B05B 1/34*** | (2006.01) |
| *A61M 11/06* | (2006.01) |
| *A61M 11/08* | (2006.01) |
| *A61M 15/00* | (2006.01) |

(52) U.S. Cl.

CPC ................. *A61M 11/00* (2013.01); *B05B 1/14* (2013.01); *B05B 1/3436* (2013.01); *A61M 11/06* (2013.01); *A61M 11/08* (2013.01); *A61M 15/009* (2013.01); *A61M 2206/16* (2013.01)

(58) Field of Classification Search

USPC ............ 128/200.14, 200.18–200.21, 203.12, 128/207.14; 604/275, 514

See application file for complete search history.

(56) References Cited

U.S. PATENT DOCUMENTS

| | | | | |
|---|---|---|---|---|
| 2,994,483 A | | 8/1961 | Christian | |
| 3,161,196 A | | 12/1964 | Berkow | |
| 3,568,933 A | * | 3/1971 | Macguire-Cooper | B05B 1/26 239/337 |
| 4,087,050 A | * | 5/1978 | Tsuji | F23D 11/383 239/490 |
| 5,421,519 A | | 6/1995 | Woods | |
| 5,516,045 A | | 5/1996 | Baudin | |
| 5,593,661 A | * | 1/1997 | Henry | A61K 9/008 424/45 |
| 5,711,489 A | * | 1/1998 | Yanagida | B05B 5/032 239/105 |
| 5,735,465 A | * | 4/1998 | Laforcade | B05B 1/14 239/337 |
| 5,785,250 A | | 7/1998 | De Laforcade | |

(Continued)

FOREIGN PATENT DOCUMENTS

| | | |
|---|---|---|
| EP | 0 786 421 A1 | 7/1997 |
| FR | 2 467 604 A1 | 4/1981 |
| FR | 2 798 068 A1 | 3/2001 |

OTHER PUBLICATIONS

WebMD, "Nasal Sprays for Cold Relief", retrieved from http://web.archive.org/web/20100128051109/http://www.webmd.com/cold-and-flu/cold-guide/nasal-sprays-coldrelief on Jan. 28, 2010.*

(Continued)

*Primary Examiner* — Tan-Uyen (Jackie) T Ho
*Assistant Examiner* — Joseph D Boecker
(74) *Attorney, Agent, or Firm* — Flynn, Thiel, Boutell & Tanis, P.C.

(57) ABSTRACT

A nozzle unit for discharge of a pharmaceutical medium and a dispenser equipped therewith. The nozzle unit includes a common supply channel for supply of the medium and first and second discharge nozzles each having a discharge orifice for discharge of the medium supplied through the common supply channel. The nozzle unit is configured for atomized delivery of the medium and includes a first vortex chamber assigned to the first discharge nozzle and a second vortex chamber assigned to the second discharge nozzle for the purpose of atomizing.

15 Claims, 3 Drawing Sheets

(56) References Cited

U.S. PATENT DOCUMENTS

| | | | | |
|---|---|---|---|---|
| 5,813,785 | A | 9/1998 | Baudin et al. | |
| 6,378,787 | B1 * | 4/2002 | Buchi | F23D 11/26 239/406 |
| 6,516,795 | B1 | 2/2003 | Bougamont et al. | |
| 7,007,867 | B1 * | 3/2006 | Drapeau | B05B 1/3436 239/333 |
| 8,191,802 | B2 * | 6/2012 | Khan | B05B 1/14 239/548 |
| 8,757,146 | B2 * | 6/2014 | Hoekman | A61M 15/00 128/200.21 |
| 2002/0104898 | A1 * | 8/2002 | Bonningue | B05B 7/2421 239/311 |
| 2003/0025001 | A1 * | 2/2003 | De Laforcade | B05B 1/26 239/333 |
| 2004/0044303 | A1 * | 3/2004 | Katz | B05B 11/0091 604/19 |
| 2005/0224605 | A1 * | 10/2005 | Dingle | F02B 23/0669 239/533.2 |
| 2005/0284965 | A1 * | 12/2005 | Schneider | F02M 61/186 239/533.12 |
| 2006/0097082 | A1 * | 5/2006 | Goenka | F02M 61/1806 239/533.14 |
| 2008/0093392 | A1 * | 4/2008 | Abduljalil | B05B 1/3426 222/394 |
| 2013/0214063 | A1 * | 8/2013 | Ryon | F23R 3/28 239/463 |
| 2013/0306757 | A1 * | 11/2013 | Parmentier | B05B 1/3436 239/404 |
| 2014/0144888 | A1 * | 5/2014 | Toyota | B05B 7/226 219/76.16 |

OTHER PUBLICATIONS

Search Report of European Patent Office issued in European Patent Application No. 13 152 436.5 dated May 14, 2013 with English translation of category of cited documents (9 pages).

* cited by examiner

NOZZLE UNIT AND DISPENSER

FIELD OF THE INVENTION

The invention relates to a nozzle unit for discharging a medium with a supply channel for supplying the medium and with at least a first and a second discharge nozzle each having one discharge orifice for discharging the medium supplied through the common supply channel. Furthermore, the invention also relates to a dispenser comprising such a nozzle unit.

BACKGROUND OF THE INVENTION

Generic dispensers and dispensers according to the present invention are used for discharging or dispensing pharmaceutical media. While most of the well-known dispensers for discharge of pharmaceutical media include but one discharge nozzle having one discharge orifice, in particular cases there is also need to discharge the pharmaceutical medium through multiple discharge orifices of multiple discharge nozzles simultaneously. Dispensers designed for that purpose are well-known from EP 0786421, U.S. Pat. No. 3,161,196 and FR 2467604 A1, for example. Said generic dispensers are provided with multiple discharge orifices directly connected to the common supply channel.

However, administration of pharmaceutical media using such dispensers has in general not proved to achieve the desired effect, since with the known devices the medium is discharged in a largely non-atomized condition.

In the prior art, a variety of dispensers are well-known which include swirling devices to swirl or whirl the medium before its discharge. Said swirling devices possess a vortex chamber where the medium is introduced in such a manner that the medium is provided with a twist within the chamber and thus before its discharge to allow a discharge in the form of a conical spray jet.

To achieve a discharge grade of similar good quality, even with generic dispensers including more than one discharge orifice, attempts have been made to connect a common vortex chamber upstream of the discharge orifices. However, said means have proved to result in a structure that is complex and laborious to produce, and also does not seem to yield a spray jet of satisfactory quality grade.

SUMMARY OF THE INVENTION

Therefore, the object of the invention is to further develop a generic nozzle unit to the effect that said unit is adapted to deliver at least two spray jets in a good quality grade. Furthermore, an object of the invention is to provide a dispenser including such a nozzle unit.

According to the invention, the underlying object is solved in that the nozzle unit is configured for atomized delivery of the medium and includes a first vortex chamber assigned to a first discharge nozzle and a second vortex chamber assigned to a second discharge nozzle for the purpose of atomizing.

Thus, what is provided according to the invention is that both the discharge orifices each have a distinct vortex chamber connected upstream and each chamber is supplied with medium from the common supply channel. Within said vortex chambers, the supplied medium is imparted the desired twist and discharged through both the discharge orifices.

Although so far and in the following a focus is on a design wherein two discharge orifices and thus also two vortex chambers are provided, a nozzle unit according to the invention and a dispenser according to the invention may of course as well be provided with further discharge nozzles including further discharge orifices and further vortex chambers. Preferably, all discharge nozzles are presumed each to include one discharge orifice and a distinct vortex chamber connected upstream of said discharge orifice.

A vortex chamber in terms of the present invention is a chamber defined by parts that are immobile one relative to the other and that include at least one inlet and one outlet aligned in the direction of the discharge orifice. The shape design of said vortex chamber is such that the liquid medium entering the vortex chamber under high pressure through the inlet is provided with a twist therein, before streaming out of the vortex chamber in the direction of the outlet. Preferably, said twist is effected by an approximately circular cylindrical shape of the vortex chamber and an inflow direction of the medium differing from the radial direction. The axis, the medium in the vortex chamber is rotating about and which in case of circular cylindrical vortex chambers is coincident with the cylinder axis, is referenced by the term vortex chamber axis in the following.

Due to the design according to the invention provided with in each case one vortex chamber per discharge nozzle, the advantageous spray pattern can be generated in the above mentioned manner. Since there is in each case only one discharge orifice fed with the medium that has been provided with a twist in a vortex chamber, there is no tradeoff required in view of supply of the medium from the vortex chamber to the discharge orifice.

However, said design including a multitude of vortex chambers entails the problem of increased manufacturing cost as a matter of principle.

In particular considering the aspect of cost-efficient production, an advantage appears in the feature that the nozzle unit includes a basic component in which the supply channel is provided at least in sections, the nozzle unit further includes at least one top component which includes at least the discharge orifice of the first discharge nozzle, and the first vortex chamber of the first discharge nozzle is delimited by walls of the basic component and by walls of the top component.

Thus, the nozzle unit according to the invention comprises preferably a component, the basic component, to form at least one end part of the supply channel. Said basic component together with a second component, the top component, delimit at least one of the vortex chambers. Since said chamber has to be delimited to the exterior by walls except for said inlets and said outlet, at least two components need to be used for manufacturing reasons. According to said advanced development, these are the two components that have to be provided anyway to build the supply channel and to build the discharge orifices.

Thus, in the extreme case and in the ideal case, the nozzle unit according to the invention can be composed of only two components, namely the basic component and the top component.

Indeed, in principle there is an option to use a plurality of top components, each provided with a discharge orifice and defining a vortex chamber together with the basic component. However, an advantageous design includes only one top component, comprising multiple, preferably all, discharge orifices of the discharge nozzles, and preferably delimiting an equal number of vortex chambers.

The top component and the basic component are preferably configured to be connected one to the other directly by a force-fit or a form-fit connection. In that context, press-fit connections and snap-on connections may be put up. Even a material engagement connection by welding the components or bonding the components is possible as a matter of principle. In general, plastics are a convenient material for the basic component and the one or more top components. The structure of the nozzle unit allows manufacturing of both the plastic parts that constitute the top component and the basic component of the nozzle unit in the form of injection moulded plastic parts to be readily demoulded.

Vortex chambers for the nozzle units according to the invention have a flow deflecting geometry configured such that it is capable of deflecting the medium and imparting said twist. As already explained, to that aim said flow deflecting geometries comprise in particular a circular cylindrical wall or any other curved walls, along which the medium is flowing with a simultaneous change of direction. A particular advantage appears in the feature that said flow deflecting geometries adapted to deflection of the medium stream are provided on an interior side of the top component.

For instance, on an interior side of the top component facing the basic component a surface can be provided which upon assembly is flush resting against the basic component, with said surface being provided with recesses that form the flow deflecting geometries. Such a structure may be achieved in a particularly simple manner during a manufacturing procedure of the top component. All the same, in principle there is even an option to provide the corresponding geometries at the basic component instead of the top component, and there in particular on an end face wall. In the same way as with the top component, the flow deflecting geometries may be achieved in a manner that in a surface provided on the respective component, recesses are provided, whereby zones surrounding said recesses are embossed as compared to the recesses, and can be part of the flow deflecting geometries.

In the context of designing the top component to include the flow deflecting geometries, a further particularly advantageous feature is in that the basic component, at least in a zone adjacent to the top component, is formed by a tubular section, wherein an annular end face of said tubular section delimits the first and the section vortex chambers. Preferably, said tubular section is formed to have a circular cross-section. The vortex chambers are arranged on the top component preferably in such a manner that they are located interposed between the internal diameter and the external diameter of said tubular section, so that the end face of the latter can close the vortex chambers. In this respect, the end face does not mandatorily need to be completely planar. It can also have other shape designs, even in the shape of a cone section, for example.

The discharge direction through the first discharge nozzle and the discharge direction through the second discharge nozzle are preferred to form an angle between 0° and 150°. Preferred is a diverging discharge direction, and thus a formed angle of more than 0°, and particularly of more than 10° is preferred. For the particularly relevant application purpose of a pharyngeal spray dispenser, an angle between 45° and 90° is considered to be an ideal angle. In the context of the present invention, the discharge direction is meant to be the central axis of the spray cone. The specific alignment of the discharge directions should be selected according to the purpose of application.

In cases where the discharge directions diverge, one of two preferred options may be selected with regard to the vortex chamber axis of the vortex chambers. One possible option is that the vortex chamber axis of the vortex chambers forms an angle of more than 0° to the discharge directions of the respective nozzles, to allow another deflection of the medium between the vortex chamber and the discharge orifice. As a result, the vortex chambers can be designed in particular in a way that the respective vortex chamber axes extend in parallel to each other. Said feature is ideal in the context of a planar end face of the basic component. In addition, demoulding during a manufacturing procedure, in particular of the top component, is facilitated. As an alternative to such a design, the vortex chamber axes of the vortex chambers can also extend in parallel or even aligned to the discharge direction of the respective discharge nozzle. Indeed, said feature is a somewhat impeding factor during production. However, said feature prevents that the medium is again deflected after or during output from the vortex chamber, whereby the quality grade of the spray jet could be affected.

As already explained above, the vortex chambers are fed with medium via the supply channel. For that purpose, at least one inlet channel is required to connect the supply channel to the vortex chamber and to end in the vortex chamber preferably in a non-radial, in particular tangential configuration. To improve the spray jet, a preferred variant features that at least in view of one of the vortex chambers at least two inlet channels are provided which end in said vortex chamber. Preferably, said inlet channels are branched off from an annular channel surrounding the vortex chamber, said annular channel being fed by the supply channel. Using two inlet channels allows the medium to enter the vortex chamber more uniformly, and thus an improved spray jet is formed. The surrounding annular channel is effective to obtain the uniform feeding of the vortex chamber via the at least two inlet channels in a particularly advantageous manner. Of course, as a matter of principle, even without an annular chamber, the feeding of more than one inlet channel into the same vortex chamber is feasible.

Furthermore, the present invention is related to a dispenser for discharging pharmaceutical media in an atomized condition. According to the invention said dispenser includes a nozzle unit of a previously described type.

In particular, a dispenser according to the invention can be configured to be a pharyngeal spray dispenser, and for that purpose can include a section with a tubular shape and extending preferably radial to a direction of actuation of the dispenser having a length of preferably at least 20 mm, to be introduced into the mouth of a patient. Said tubular section is preferred to be the basic component of the nozzle unit as described. Depending on the purpose of application, in particular lengths of more than 30 mm or even more than 40 mm may be convenient.

With such a pharyngeal spray dispenser, the two discharge nozzles and the directing alignment of the discharge occurring through both the nozzles allows the discharge to be effected past the left and the right of the uvula of the patient. Such an application is more comfortable for the patient and finally serves to correct administration of the pharmaceutical medium.

The pharmaceutical medium per se can preferably be a medicament to treat common cold diseases.

BRIEF DESCRIPTION OF THE DRAWINGS

Further aspects and advantages of the invention will become clear from the claims and the following description of preferred embodiments of the invention as illustrated with reference to the drawings, in which:

DETAILED DESCRIPTION

Figure 1A:
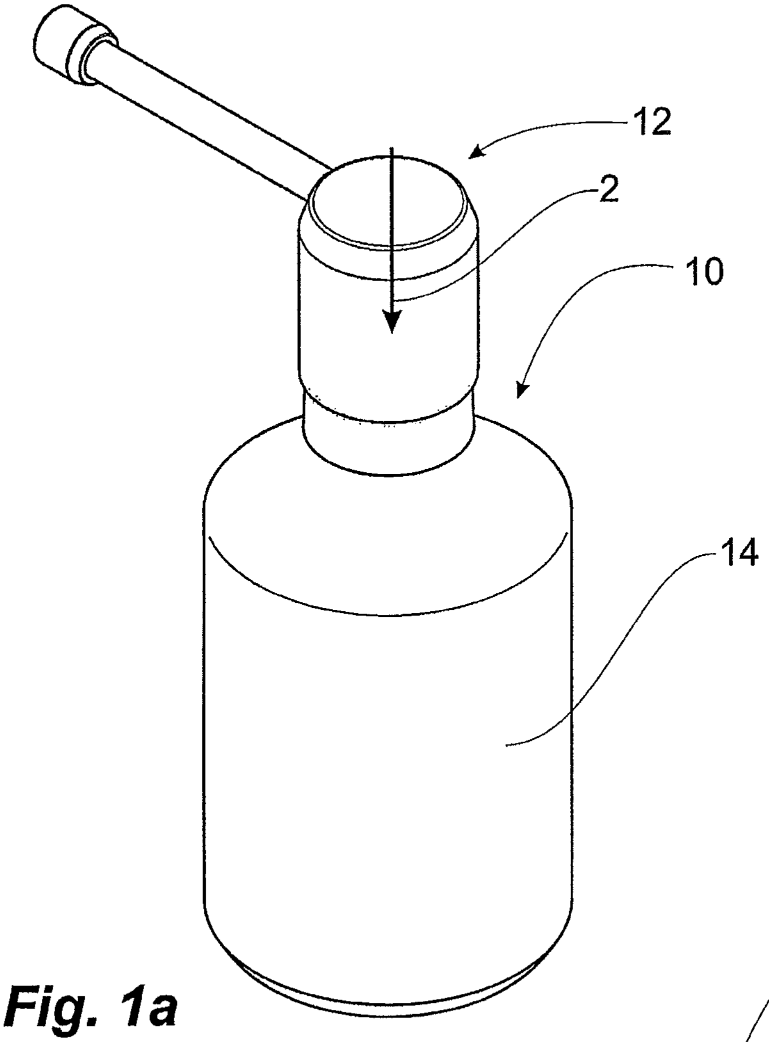
FIGS. 1*a* and 1*b* show a dispenser according to the invention and the discharge head thereof, respectively.
Figure 1B:
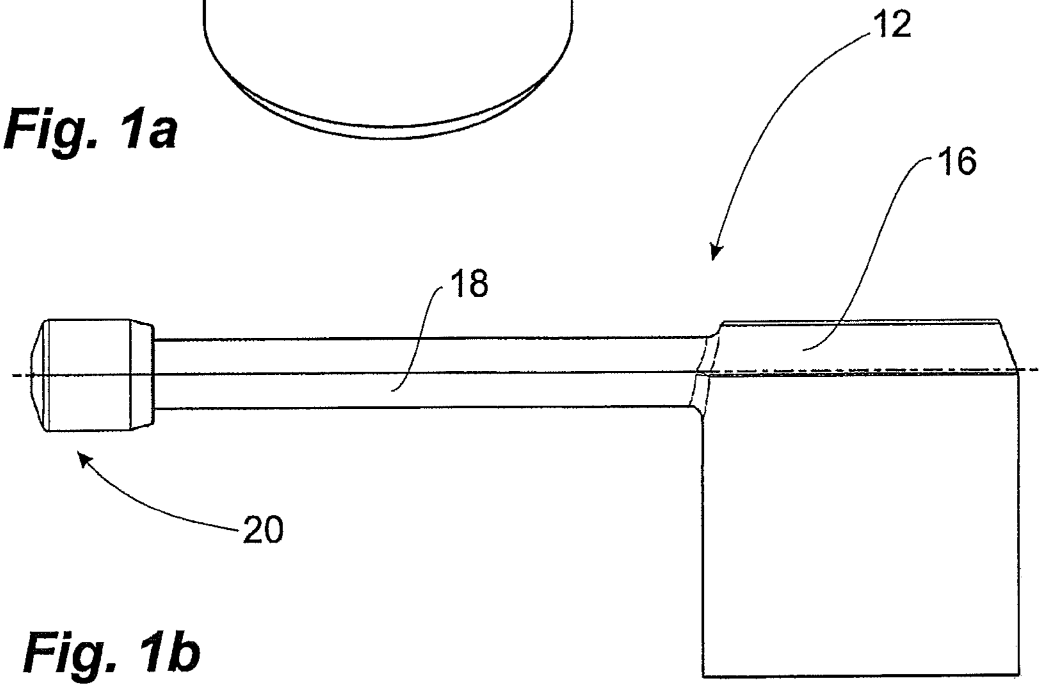

FIGS. 1*a* and 1*b* show a dispenser 10 according to the invention including a discharge head 12. Said dispenser 10 includes a reservoir 14 for storage of a pharmaceutical medium that is to be discharged. Said discharge head 12 in its entirety is displaceable relative to said reservoir 14 in the direction of an actuation direction 2, whereby a pump device (not illustrated) is actuated to draw medium from the reservoir 14 into the discharge head 12.

The discharge head 12 is illustrated in FIG. 1*b* in a side elevation view. Said head comprises an operation handle 16 configured in the form of a knob and a longitudinal spout-type applicator 18 with a nozzle unit 20 provided at the end thereof for atomized output of the medium.

Below, diverse variants of embodiments, in particular of the nozzle unit 20 are presented.

Figure 2A:
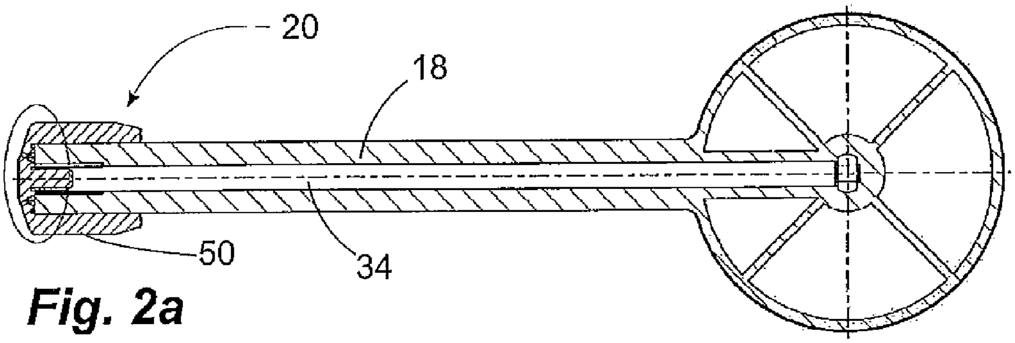
FIGS. 2*a* to 2*d* show embodiments of the discharge head according to FIGS. 1*a* and 1*b* including a first embodiment of a nozzle unit according to the invention.
Figure 2B:
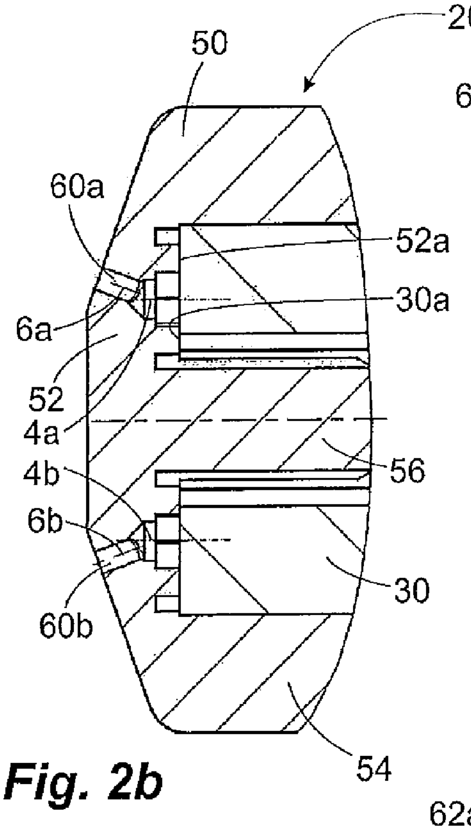
Figure 2C:
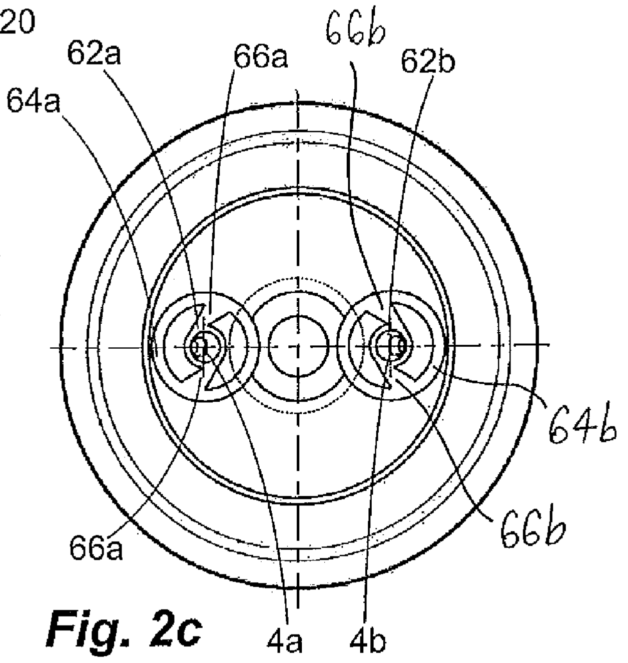
Figure 2D:
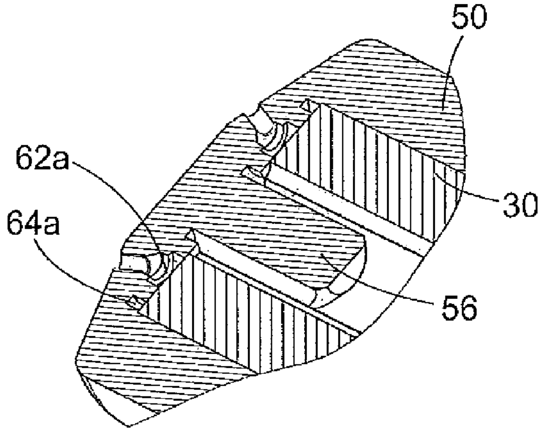

The nozzle unit 20 illustrated in FIGS. 2*a* to 2*c* is composed of a tube 30 of the applicator 18 constituting a basic component, and a top or cap component 50 fitted on the end side of said tube 30. Said top component 50 has a sleeve-type structure including a collar 54 projecting from an end face 52, and said collar can be fixed via a force fit to the exterior side of the tube 30, for example. Furthermore, the top component 50 includes a centric pin-type extension 56 extending into the tube 30.

The end face 52 is traversed by two discharge orifices 60*a*, 60*b*. On the interior side 52*a* of the end face 52 the discharge orifices 60*a*, 60*b* surround various recesses. Said recesses each comprise, in particular in the design as illustrated in FIG. 2*c*, primarily one recess acting as a vortex chamber 62*a*, 62*b* surrounded by an annular groove forming an annular channel 64*a*, 64*b*. From each said annular channel 64*a*, 64*b* two inlet channels 66*a*, 66*b* extend into the vortex chamber 62*a*, 62*b*. Said inlet channels 66*a*, 66*b* run essentially tangential relative to a vortex main axis 4*a* and 4*b*, respectively, such that the medium entering from the annular channel 64*a*, 64*b* and flowing into the corresponding vortex chamber 62*a*, 62*b* is deflected to a rotatory movement. In the direction of the tube 30, the vortex chambers 62*a*, 62*b* and part of the respective annular channels 64*a*, 64*b* are closed by an end face 30*a* of the tube 30. The medium drawn through the supply channel 34 in the direction of the nozzle unit 20 can flow past the pin-type extension 56 directly and initially through the not closed part of the annular channels 64*a*, 64*b* only to the corresponding annular channel 64*a*, 64*b*. To illustrate this, the internal diameter of the tube 30 at the end face 30*a* thereof is shown in a dashed line in FIG. 2*c*. Access to the annular channels 64*a*, 64*b* is provided at the interior of said internal diameter. From the annular channels 64*a*, 64*b* the liquid medium passes through the inlet channels 66*a*, 66*b* into the vortex chambers 62*a*, 62*b*, and is then output through the discharge orifices 60*a*, 60*b* in the form of a conical spray jet.

The illustrated design allows realization of two discharge nozzles each including a distinct vortex chamber 62*a*, 62*b* using only two components 30, 50. In addition said components 30, 50 are very easy to produce due to their simple design. Due to the relative spacing of the vortex chambers 62*a*, 62*b* according to the diameter of the tube 30, the flow deflecting geometry, which can readily be produced on the top component 50 side, is closed by the end face 30*a* of the tube 30, so that the desired liquid path is thereby completed with a vortex chamber between the supply channel 34 and the discharge orifices 60*a*, 60*b*.

As can be seen in particular from FIG. 2*a*, the discharge directions or axes 6*a*, 6*b* of both the discharge orifices 60*a*, 60*b* are arranged diverging to each other, in order to form two separate spray jets, for example, which are output passing on both sides of a palate. Due to the orientations of the vortex chamber axes 4*a* and 4*b* parallel relative to each other, there is however a deflection required in the vicinity of the outlet orifices.

Figure 3A:
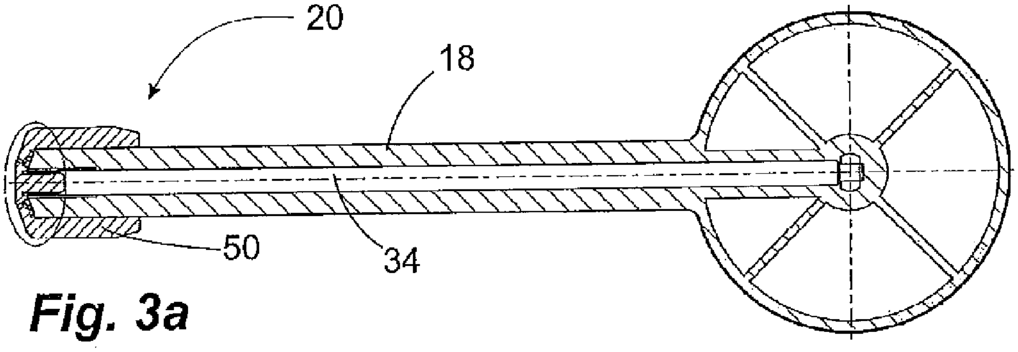
FIGS. 3*a* to 3*c* show embodiments of the discharge head according to FIGS. 1*a* and 1*b* including a second embodiment of a nozzle unit according to the invention.
Figure 3B:
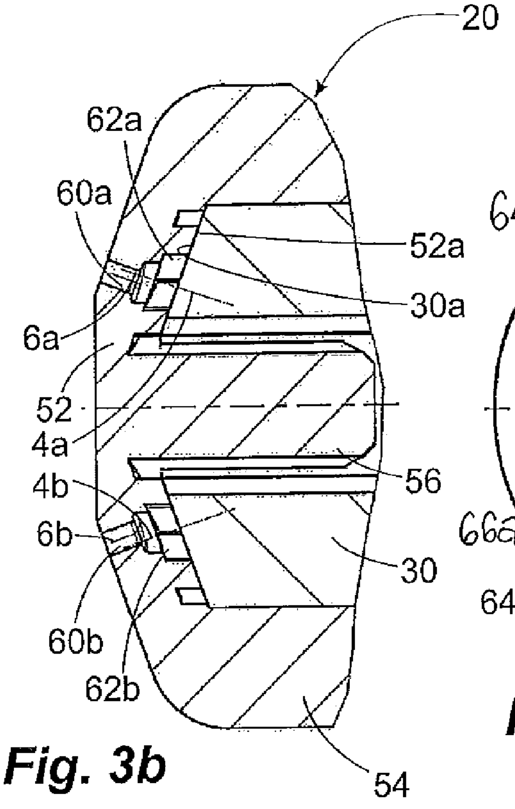
Figure 3C:
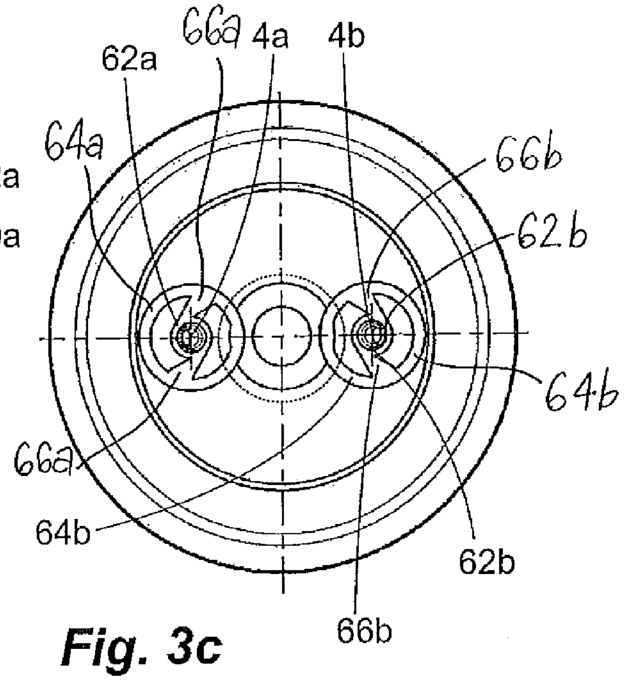

In the embodiment of FIGS. 3*a* and 3*b*, the extent of said deflection is reduced by the feature that the vortex chambers 62*a*, 62*b* per se are oriented in an angular position. The end face 30*a* of the tube 30 is herein configured in the shape of a cone section including the corresponding angle.

Figure 4A:
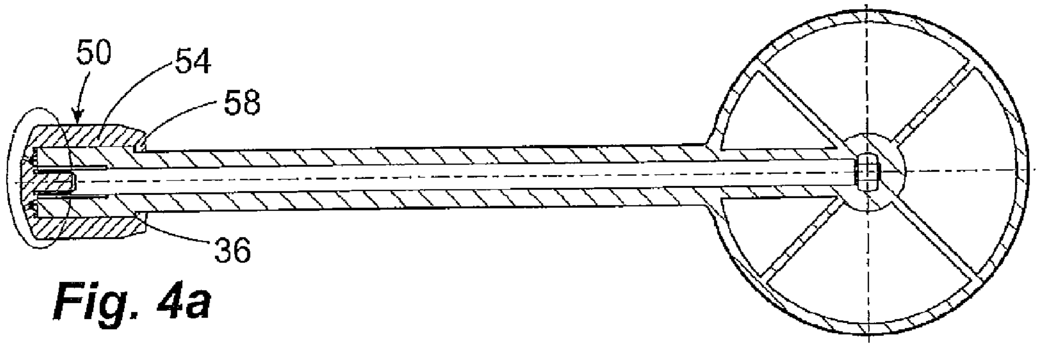
FIG. 4*a* shows embodiments of the discharge head according to FIGS. 1*a* and 1*b* including a third embodiment of a nozzle unit according to the invention.

In the embodiment of FIG. 4*a*, the structure is essentially corresponding to that according to FIG. 2*a*. However, other than shown therein, the top component 50 is provided not to be fixed by a press-fit connection or by welding to the tube 30, but by a form-fit coupling. For that purpose, the collar 54 is provided with snap tabs 58 engaging behind a shoulder 36 on the tube 30.

The invention claimed is:

1. A nozzle unit for atomized discharge of a pharmaceutical medium, said nozzle unit comprising:

a first component including a common supply channel;

first and second discharge nozzles including respective first and second discharge orifices through which medium supplied from the common supply channel is discharged, the first discharge orifice and the second discharge orifice defining respective first and second central discharge axes along which medium is discharged from the nozzle unit, the first and second central discharge axes forming an angle having a value greater than zero degrees and a maximum of 150 degrees;

a first vortex chamber in communication with the first discharge orifice of the first discharge nozzle for atomizing delivery of the medium from the nozzle unit and a second vortex chamber in communication with the second discharge orifice of the second discharge nozzle for atomizing delivery of the medium from the nozzle unit, the first and second vortex chambers each having a shape which induces rotation in the medium about respective first and second vortex chamber axes, the first and second vortex chamber axes forming an angle having a value of zero degrees; and a second component including the first and second discharge orifices of the first and second discharge nozzles, the first and second vortex chambers being delimited by walls of the first and second components.

2. The nozzle unit according to claim 1, wherein the value of the angle defined by the first and second central discharge axes is between at least 45 degrees and a maximum of 90 degrees.

3. The nozzle unit according to claim 1, wherein the second component has oppositely facing exterior and interior sides, and the first and second vortex chambers each include a flow-deflecting geometry defined on the interior side of the second component.

4. The nozzle unit according to claim 3, wherein the first component includes an elongate tubular portion, the tubular portion having an annular end face disposed immediately adjacent and in opposed relation with the interior side of the second component, the annular end face defining a portion of at least one of: the first vortex chamber and the second vortex chamber.

5. The nozzle unit according to claim 1, wherein the second component has oppositely facing exterior and interior sides, and the first and second vortex chambers each include a flow-deflecting geometry defined on the interior side of the second component, the first component including an elongate tubular portion having an annular end face disposed immediately adjacent and in opposed relation with the interior side of the second component, the annular end face defining boundary portions of the first and second vortex chambers.

6. The nozzle unit according to claim 5, wherein the second component is substantially sleeve-shaped and is fixed to a terminal end of the tubular portion, the second component including a projection which extends into an interior of the terminal end of the tubular portion, the first discharge orifice of the first discharge nozzle extending within the second component so as to open outwardly at one end through the exterior side of the second component and so as to open inwardly at an opposite end into the first vortex chamber, the second discharge orifice of the second discharge nozzle extending within the second component so as to open outwardly at one end through the exterior side of the second component and so as to open inwardly at an opposite end into the second vortex chamber.

7. The nozzle unit according to claim 3, wherein the interior side of the second component defines a first inlet channel having a first end in communication with the common supply channel and a second end terminating at and communicating with the first vortex chamber, and a second inlet channel having a first end in communication with the common supply channel and a second end terminating at and communicating with the second vortex chamber.

8. The nozzle unit according to claim 7, wherein the interior side of the second component defines a first annular channel surrounding the first vortex chamber and a second annular channel surrounding the second vortex chamber, the first and second annular channels being in communication with and fed medium by the supply channel, the first end of the first inlet channel terminating at and communicating with the first annular channel and the first end of the second inlet channel terminating at and communicating with the second annular channel.

9. The nozzle unit according to claim 8, wherein the interior side of the second component defines a third inlet channel having a first end terminating at and in communication with the first annular channel and a second end terminating at and communicating with the first vortex chamber, and a fourth inlet channel having a first end terminating at and in communication with the second annular channel and a second end terminating at and communicating with the second vortex chamber.

10. A dispenser for atomized discharge of pharmaceutical medium, comprising:

a reservoir configured for storing medium to be discharged;

a nozzle unit configured for discharging medium from the reservoir, the nozzle unit comprising:

a first component including a common supply channel;

first and second discharge nozzles including respective first and second discharge orifices through which medium supplied from the common supply channel is discharged, the first discharge orifice and the second discharge orifice defining respective first and second central discharge axes along which medium is discharged from the nozzle unit, the first and second central discharge axes forming an angle having a value greater than zero degrees and a maximum of 150 degrees;

a first vortex chamber in communication with the first discharge orifice of the first discharge nozzle for atomizing delivery of the medium from the nozzle unit and a second vortex chamber in communication with the second discharge orifice of the second discharge nozzle for atomizing delivery of the medium from the nozzle unit, the first and second vortex chambers each having a shape which induces rotation in the medium about respective first and second vortex chamber axes, the first and second vortex chamber axes forming an angle having a value of zero degrees; and a second component including the first and second discharge orifices of the first and second discharge nozzles, the first and second vortex chambers being delimited by walls of the first and second components.

11. The dispenser according to claim 10, wherein the dispenser is configured as a pharyngeal spray dispenser and a pharmaceutical medium for treatment of the common cold is disposed in the reservoir, the first component including a tubular section having a length of at least 20 mm for introduction into the mouth of a user.

12. A nozzle unit for atomized discharge of a pharmaceutical medium, said nozzle unit comprising:

a first component defining therein a supply channel;

a second component fixed to the first component and defining therein first and second discharge nozzles including respective first and second discharge orifices in communication with the supply channel for discharging pharmaceutical medium from the supply channel to an environment, the first discharge orifice and the second discharge orifice defining respective first and second central discharge axes along which pharmaceutical medium is discharged from the nozzle unit to the environment, the first and second central discharge axes together forming an angle having a value greater than zero degrees and a maximum of 150 degrees; and a first vortex chamber in communication with the first discharge orifice of the first discharge nozzle for atomizing delivery of the pharmaceutical medium from the nozzle unit and a second vortex chamber in communication with the second discharge orifice of the second discharge nozzle for atomizing delivery of the pharmaceutical medium from the nozzle unit, the first and second vortex chambers each having a shape which induces rotation in the pharmaceutical medium about respective first and second vortex chamber axes, the first and second vortex chamber axes together forming an angle having a value which is different from the angle defined by the first and second discharge axes, the first and second components having respective surfaces disposed in face-to-face opposed relation with one another, the first and second vortex chambers being defined between the opposed surfaces of the first and second components.

13. The nozzle unit according to claim 12, wherein the second component has oppositely facing exterior and interior sides and the surface of the second component is disposed on the interior side, and the first and second vortex chambers each include a flow-deflecting geometry defined on the interior side of the second component.

14. The nozzle unit according to claim 13, wherein the first component includes an elongate tubular portion in which the supply channel is disposed, the surface of the first component being defined on an annular end face of the tubular portion disposed immediately adjacent and in opposed relation with the surface defined on the interior side of the second component, the annular end face defining respective portions of the first and second vortex chambers.

15. The nozzle unit according to claim 12, wherein the value of the angle defined by the first and second vortex chamber axes is zero degrees.

* * * * *